US011162917B2

(12) United States Patent
Liu et al.

(10) Patent No.: US 11,162,917 B2
(45) Date of Patent: Nov. 2, 2021

(54) DEVICE FOR IMPROVING GAS DETECTION IN PHOTOIONIZATION DETECTOR

(71) Applicant: HONEYWELL INTERNATIONAL INC., Morris Plains, NJ (US)

(72) Inventors: Chang Liu, Harbin (CN); Guangli Xie, Shanghai (CN); Zhiguo Wang, Shanghai (CN); Bo Chen, Shanghai (CN); Yang Zhang, Jia Ding (CN)

(73) Assignee: Honeywell International Inc., Morris Plains, NJ (US)

(*) Notice: Subject to any disclaimer, the term of this patent is extended or adjusted under 35 U.S.C. 154(b) by 0 days.

(21) Appl. No.: 16/804,066

(22) Filed: Feb. 28, 2020

(65) Prior Publication Data
US 2020/0278320 A1    Sep. 3, 2020

(30) Foreign Application Priority Data
Feb. 28, 2019    (CN) .......................... 201920254732.1

(51) Int. Cl.
*G01N 27/66*    (2006.01)
(52) U.S. Cl.
CPC .................... *G01N 27/66* (2013.01)
(58) Field of Classification Search
CPC ........................... G01N 27/66; G01N 33/0047
USPC ........................................................ 324/464
See application file for complete search history.

(56) References Cited

U.S. PATENT DOCUMENTS

| 2,901,625 | A | * | 8/1959 | Friedman | G01N 27/66 137/93 |
| 5,393,979 | A | * | 2/1995 | Hsi | G01N 27/66 250/379 |
| 5,701,009 | A |  | 12/1997 | Griffiths et al. | |
| 5,773,833 | A | * | 6/1998 | Hsi | G01N 27/64 250/379 |
| 6,225,633 | B1 |  | 5/2001 | Sun et al. | |
| 6,313,638 | B1 | * | 11/2001 | Sun | G01N 27/66 324/464 |
| 6,967,485 | B1 | * | 11/2005 | Hsueh | G01N 27/64 250/382 |
| 8,362,445 | B2 | * | 1/2013 | Short | H01J 49/162 250/423 R |
| 9,459,235 | B2 | * | 10/2016 | Soundarrajan | G01N 27/66 |
| 9,645,112 | B2 | * | 5/2017 | Chan | G01N 27/68 |

(Continued)

FOREIGN PATENT DOCUMENTS

| CN | 102072945 A | 5/2011 |
| CN | 103424465 A | 12/2013 |

(Continued)

OTHER PUBLICATIONS

Corrected Notice of Allowability dated Jul. 30, 2020 for U.S. Appl. No. 16/090,391.

(Continued)

*Primary Examiner* — Christopher P McAndrew
(74) *Attorney, Agent, or Firm* — Alston & Bird LLP

(57) ABSTRACT

The present utility model relates to a device for improving gas detection in a photoionization detector. A gas detector is provided. The device reduces interference of photoelectric noise on the reading of the gas detector for target gases such as volatile organic compounds.

10 Claims, 11 Drawing Sheets

(56) References Cited

U.S. PATENT DOCUMENTS

| | | | | |
|---|---|---|---|---|
| 2008/0220535 A1* | 9/2008 | LeBoeuf | ............ | G01N 27/305 436/164 |
| 2012/0089019 A1* | 4/2012 | Fan | ....................... | A61B 8/485 600/437 |
| 2012/0252347 A1 | 10/2012 | Chan | | |
| 2012/0279277 A1 | 11/2012 | Parusel et al. | | |

FOREIGN PATENT DOCUMENTS

| | | | | |
|---|---|---|---|---|
| CN | 205027697 | U | | 2/2016 |
| CN | 10365693 | | | 4/2020 |
| EP | 1262770 | A2 | | 12/2002 |
| EP | 2458375 | A1 | | 5/2012 |
| WO | 94/27141 | A1 | | 11/1994 |
| WO | WO-9427141 | A1 | * | 11/1994 ............ G01N 27/66 |
| WO | 2011/090433 | A1 | | 7/2011 |
| WO | 2018/022072 | A1 | | 2/2018 |

OTHER PUBLICATIONS

Corrected Notice of Allowability dated Jun. 29, 2020 for U.S. Appl. No. 16/090,391.
Extended European Search Report for Patent Application No. 20160284.4 dated Jul. 17, 2020, 11 pages.
Communication pursuant to Rules 70(2) and 70a(2) for European Patent Application No. 20160284.4 dated Sep. 7, 2020, 2 pages.
Non-Final Rejection dated Sep. 17, 2020 for U.S. Appl. No. 16/988,180.
Notice of Allowance and Fees Due (PTOL-85) dated May 11, 2020 for U.S. Appl. No. 16/090,391.
Communication pursuant to Article 94(3) for European Application No. 16753755.4, dated Mar. 12, 2020, 4 pages.
International Search Report and Written Opinion for corresponding International Application No. PCT/US2016/044614, dated Jan. 12, 2016, 14 pages.
Non-Final Rejection dated Feb. 25, 2020 for U.S. Appl. No. 16/090,391.
Notice of Grant of Patent Right for Chinese Application No. 201920254732.1, dated Jan. 17, 2020, 6 pages.
Office Action for Chinese Application No. 201920254732.1, dated Oct. 22, 2019, 3 pages.
Photoionization Detectors, Chapter 6, https://web.archive.org/web/20050119175603/http://intlsensor.com/pdf/photoionization.pdf, Retrieved Dec. 5, 2018, 9 pages, Jan. 16, 2005, 9.
Communication about intention to grant a European patent dated Apr. 22, 2021 for EP Application No. 16753755.4, 5 pages.
Examination Report No. 2 issued in Australian Application No. 2020201513 dated Apr. 1, 2021, 5 pages.
Annex to the Communication pursuant to Article 94(3) for European Application No. 16753755.4, dated Mar. 12, 2020, 2 pages.
Communication Pursuant to Article 94(3) dated Mar. 12, 2020 for EP Application No. 16753755.4, 2 pages.
Intention to grant issued in European Application No. 16753755.4 dated Nov. 11, 2020, 5 pages.
Jun et al. "Technology and Evaluation of Foreign Chemical Poison Detector," National Defense Industry Press, p. 322, 326.
Notice of Allowance and Fees Due (PTOL-85) dated Dec. 2, 2020 for U.S. Appl. No. 16/988,180.
Notice of Allowance and Fees Due (PTOL-85) dated Dec. 18, 2020 for U.S. Appl. No. 16/988,180.
Notice of Allowance and Fees Due (PTOL-85) dated Jan. 26, 2021 for U.S. Appl. No. 16/988,180.
Office Action issued in Chinese Application No. 201680085323.2 dated Nov. 27, 2020, 24 pages.
Extended European Search Report issued in European Application No. 21153809.5 dated Apr. 26, 2021, 9 pages.
Decision to grant a European patent received for European Application No. 16753755.4, dated Aug. 5, 2021, 2 pages.

\* cited by examiner

DEVICE FOR IMPROVING GAS DETECTION IN PHOTOIONIZATION DETECTOR

CROSS-REFERENCE TO RELATED APPLICATIONS

This application claims the benefit of Chinese Patent Application No. 201920254732.1, filed 28 Feb. 2019, the disclosure of which is herein incorporated by reference in its entirety.

TECHNICAL FIELD

The present utility model relates to a gas detector device.

BACKGROUND

Gas detectors are commonly used to detect the existence of various target gases such as volatile organic compounds. The applicant has found many defects and problems related to the conventional gas detector. Through application efforts, originality, and innovation, many of these found problems have been solved by developing solutions included in the embodiments of the present invention, many of which are described in detail herein.

SUMMARY

Generally, the embodiments of the present invention provided herein comprises a method, device, and system for monitoring a target gas, and a computer program product. A gas detector for monitoring a target gas is provided, the gas detector comprising: a gas inlet; an ultraviolet (UV) lamp; a pair of electrically biased electrodes provided between the gas inlet and the UV lamp; and a processor, the processor communicating with the pair of electrically biased electrodes. The processor may be configured to, when the UV lamp is in a first mode and the target gas is prevented from entering the gas inlet, determine a deviation, the first mode of the UV lamp being an operating mode thereof, so that UV light is emitted from the UV lamp, and the deviation, when the pair of electrically biased electrodes are exposed to the UV lamp in the first mode and are prevented from being exposed to the target gas, being associated with an electrode signal generated by the pair of electrically biased electrodes; and when the gas inlet is open to the target gas, a calibrated output reading based on the deviation is computed, the calibrated output reading, when the pair of electrically biased electrodes are exposed to the UV lamp in the first mode and are exposed to the target gas, being associated with the electrode signal generated by the pair of electrically biased electrodes.

In some embodiments, the target gas may be prevented from entering the gas inlet by providing a calibration filter in the gas detector, inletting a calibration gas, or adopting a combination thereof. In some embodiments, the deviation may be subtracted from a detector signal obtained from the electrode signal generated by the pair of electrically biased electrodes, when exposed to the UV lamp in the first mode and exposed to the target gas. In some embodiments, the electrode signal that may be generated by the pair of electrically biased electrodes, when exposed to the UV lamp in the first mode and prevented from being exposed to the target gas, is formed by at least part of the pair of electrically biased electrodes which are ionized when exposed to the UV light emitted from the UV lamp. In some embodiments, the deviation may be determined by averaging a plurality of detector signals, and the plurality of detector signals are generated by a plurality of electrode signals generated by the pair of electrically biased electrodes when exposed to the UV lamp in the first mode and prevented from being exposed to the target gas.

In some embodiments, the UV lamp may comprise a second mode, the second mode is a non-operating mode thereof, so that photons are not emitted from the UV lamp, and the processor is configured to determine an absolute zero level when the UV lamp is in the second mode. The calibrated output reading may be computed based on the absolute zero level.

In some embodiments, the processor may be configured to determine the deviation after a predetermined period of time, after a specified event occurs, as needed or according to a combination thereof. In some embodiments, the processor may be configured to update the deviation after a predetermined period of time, after a specified event occurs, as needed or according to a combination thereof.

In some embodiments, the processor may be configured to determine the absolute zero level after a predetermined period of time, after a specified event occurs, as needed or according to a combination thereof. The processor may be configured to update the absolute zero level after a predetermined period of time, after a specified event occurs, as needed or according to a combination thereof.

In some embodiments, the calibrated output reading may represent a concentration of the target gas in an external environment in unit of parts per billion. In some embodiments, the target gas is a volatile organic compound. In some embodiments, the gas detector may comprise a UV shielding cover.

The embodiment of the present disclosure further relates to a method for monitoring a target gas by using a gas detector. The method may comprise: determining a derivation when a UV lamp is in a first mode and a target gas is prevented from entering a gas inlet of the gas detector, the first mode of the UV lamp being an operating mode of the UV lamp so that UV light is emitted from the UV lamp, and the deviation, when the pair of electrically biased electrodes are exposed to the UV lamp in the first mode and are prevented from being exposed to the target gas, being associated with an electrode signal generated by the pair of electrically biased electrodes; and when the gas inlet is open to the target gas, computing a calibrated output reading based on the deviation, the calibrated output reading, when the pair of electrically biased electrodes are exposed to the UV lamp in the first mode and are exposed to the target gas, being associated with the electrode signal generated by the pair of electrically biased electrodes.

In some embodiments, the target gas may be prevented from entering the gas inlet by providing a calibration filter in the gas detector, inletting a calibration gas, or adopting a combination thereof. In some embodiments, the step of computing a calibrated output reading may comprise subtracting the deviation from a detector signal obtained from the electrode signal generated by the pair of electrically biased electrodes, when exposed to the UV lamp in the first mode and exposed to the target gas.

In some embodiments, the electrode signal that is generated by the pair of electrically biased electrodes, when exposed to the UV lamp in the first mode and prevented from being exposed to the target gas, may be formed by at least part of the pair of electrically biased electrodes which are ionized when exposed to the UV light emitted from the UV lamp.

In some embodiments, the step of determining a deviation may comprise averaging a plurality of detector signals, and the plurality of detector signals are generated by a plurality of electrode signals generated by the pair of electrically biased electrodes when exposed to the UV lamp in the first mode and prevented from being exposed to the target gas.

In some embodiments, the UV lamp may comprise a second mode, the second mode is a non-operating mode of the UV lamp, so that photons are not emitted therefrom, and the method may comprise determining an absolute zero level when the UV lamp is in the second mode and computing the calibrated output reading based on the absolute zero level.

In some embodiments, the method may comprise determining the deviation after a predetermined period of time, after a specified event occurs, as needed, or according to a combination thereof. In some embodiments, the method may comprise updating the deviation after a predetermined period of time, after a specified event occurs, as needed, or according to a combination thereof.

In some embodiments, the method may comprise determining the absolute zero level after a predetermined period of time, after a specified event occurs, as needed or according to a combination thereof. In some embodiments, the method may comprise updating the absolute zero level after a predetermined period of time, after a specified event occurs, as needed, or according to a combination thereof.

In some embodiments, the gas detector may comprise at least one UV shielding cover adjacent to the pair of electrically biased electrodes. In some embodiments, the target gas may be a volatile organic compound.

Details of one or a plurality of the embodiments of the subject described in this description are set forth in the accompanying drawings and the following description. From the description, the accompanying drawings and the claims, other features, aspects and advantages of the subject will become apparent.

BRIEF DESCRIPTION OF THE DRAWINGS

The accompanying drawings will be described below and are not necessarily drawn to the scale.

DETAILED DESCRIPTION

Figure 1:
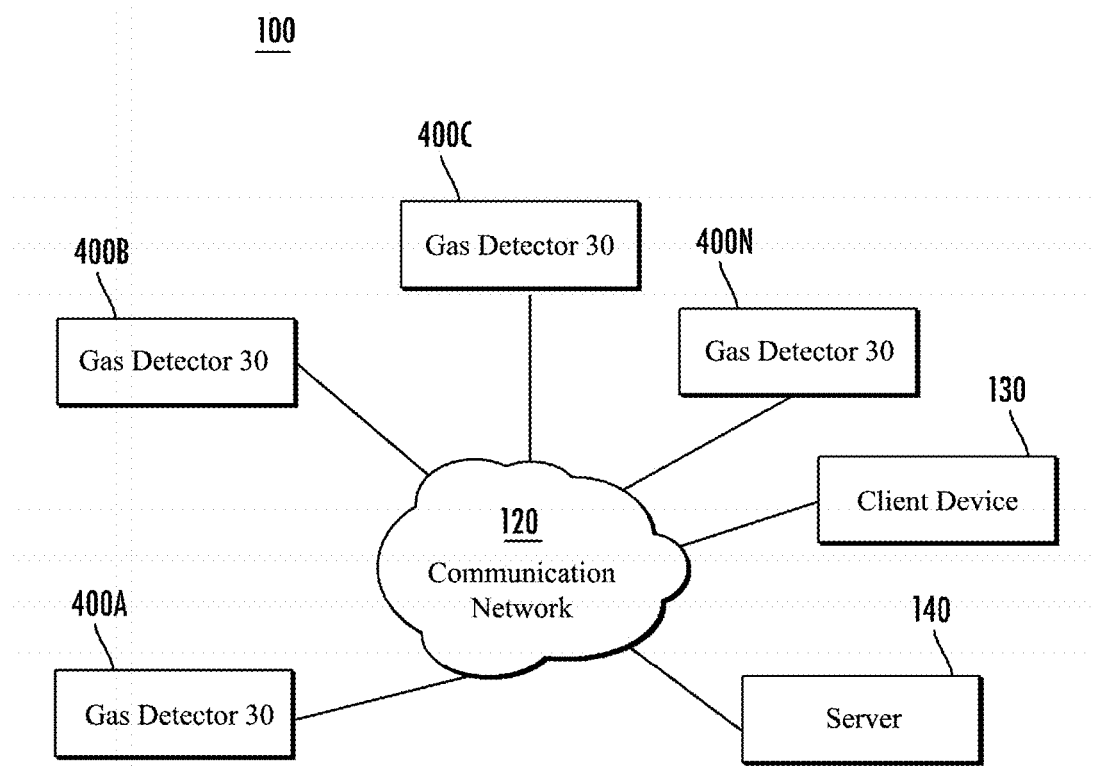
FIG. 1 illustrates an exemplary system according to some embodiments discussed herein.

Some embodiments of the present invention will be more comprehensively described below with reference to the accompanying drawings, which illustrate some, but not all, of the embodiments of the present invention. In fact, the present invention may be implemented in many different ways and should not be interpreted as limited to the embodiments described herein; instead, these embodiments are provided so that the present disclosure will meet the applicable legal requirements. The same reference sign always refers to the same component.

As used herein, the terms "data", "content", "digital content", "digital content object", "information" and similar terms may be used interchangeably to refer to data that can be transmitted, received and/or stored according to the embodiments of the present invention. Therefore, no such term should be used to limit the spirit and scope of the embodiments of the present invention. In addition, as described herein, in the situation that one device receives data from another device, it should be understood that data may be received directly from another device or indirectly received through one or a plurality of intermediate devices (such as one or a plurality of servers, relays, routers, network access points, base stations, hosts and repeaters), which are sometimes referred to as "network" herein. Similarly, as described herein, in the situation that one device transmits data to another device, it should be understood that data may be transmitted directly to another device or indirectly transmitted through one or a plurality of intermediate devices (such as one or a plurality of servers, relays, routers, network access points, base stations, hosts, and repeaters).

The term "comprise" means including but not limited to, and should be interpreted in a manner generally used in the context of the patent. The use of "comprising", "including", and broader terms should be understood to provide a support to narrow terms such as "consisting of", "substantially consisting of", and "substantially formed by".

The phrases "in one embodiment", "according to one embodiment" and the like generally mean that specific features, structures or features following the phrases may be included in at least one embodiment of the present invention, and may be included in more than one embodiment of the present invention (importantly, these phrases do not necessarily refer to the same embodiment).

The term "exemplary" as used herein means "to be used as an example, for example, or for description". Any embodiment described herein as "exemplary" is not necessarily interpreted as being more preferred or advantageous than other embodiments.

As understood by one skilled in the art, when used together with numbers, the terms "about" or "approximately" and the like may indicate a specific number, or alternatively, a range close to a specific number.

If the description states that a component or feature "may", "could", "can", "should", "will", "preferably", "possibly", "generally", "alternatively", "for example", "often" or "probably" (or other such language) be/is included or have/has a feature, the specific component or feature is not required to be included or to have the feature. Such component or feature may be alternatively included in some embodiments, or may be excluded.

Various embodiments of the present disclosure relate to a system, method, and device configured to provide improved gas detection by using a photoionization detector (PID). Gas detector calibration is improved so as to achieve more consistent and accurate readings. As used herein, the terms "gas detector", "gas sensor", or "detector" may be used interchangeably.

The photoionization detector (PID) operates by radiating ultraviolet (UV) light near a pair of electrically biased electrodes to airflow coming from the environment. If target gas exists, then the UV light ionizes some gases and collects the generated ions at one or another electrode to generate current that can be amplified, filtered, and analyzed, so as to determine current magnitude representing the concentration of the target gas.

When the target gas is ionized, the electrodes may also be ionized by the UV light, resulting in computing concentration of the target gas that is inaccurate. This type of ionization is referred to as photoelectric noise. Existing gas detectors in the prior art cannot determine or consider the photoelectric noise generated by the UV lamp ionization of the electrodes. For example, the existing gas detector is calibrated when the UV lamp is turned OFF. A zero level is established when the UV lamp is turned OFF. Once the UV lamp is turned ON, the concentration of the target gas is determined based on the zero level. Therefore, any photoelectric noise generated by the UV lamp that ionizes the electrodes is incorporated into the computed concentration of the target gas, resulting in the concentration of the target gas being artificially high.

An improved gas detector and a method for detecting a target gas are provided herein. During calibration, an absolute zero level (which may be averaged over time) is determined when the UV lamp is turned OFF. Herein, the UV lamp being turned OFF may be referred to as the "second mode" of the UV lamp. Then, the UV lamp can be turned ON. Herein, the UV lamp being turned ON may be referred to as the "first mode". Moreover, the photoelectric noise of the UV light can be determined when the target gas is not ionized at all. This reading can be referred to as "deviation".

In some embodiments, when the deviation is determined, the target gas may be prevented from entering the gas detector. The target gas may be prevented by including a calibration filter in the gas detector; injecting or pulling the calibration gas through the gas detector to prevent the target gas from moving through the gas detector; preventing the target gas from moving through the gas detector using other manners; or adopting a combination thereof. Any suitable method capable of preventing the target gas from moving through the gas detector and being ionized by the UV lamp may be used.

Figure 4:
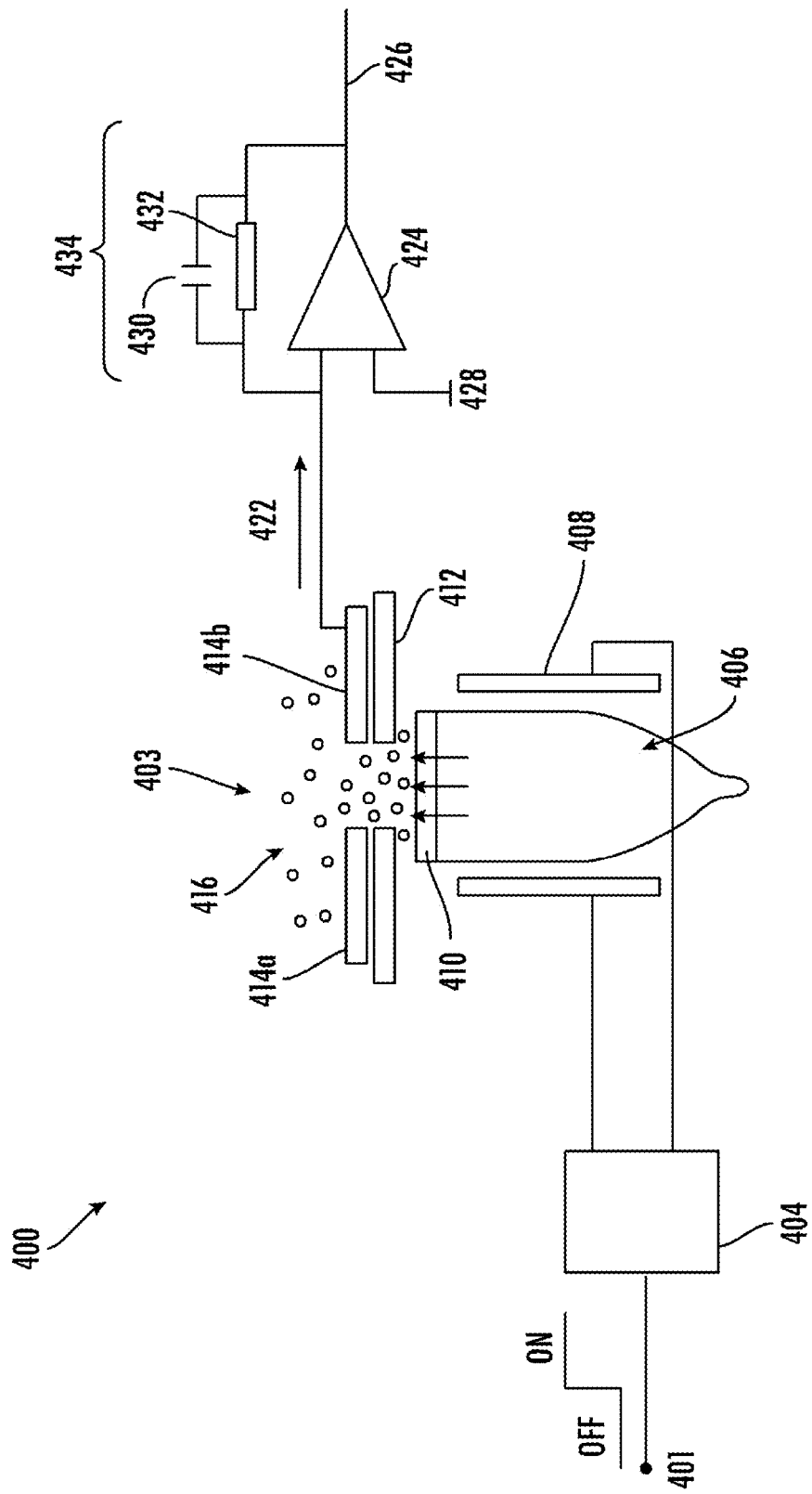
FIG. 4 illustrates an exemplary gas detector according to one embodiment disclosed herein.

Once the deviation is determined, the calibration filter or other methods for preventing the target gas from being ionized by the UV lamp may be removed or stopped, so that the target gas or the external environment that may contain the target gas can be allowed to enter the gas detector and be ionized by the UV lamp. When the gas coming from the external environment is allowed to enter the gas detector without removing the target gas, the operating mode of the gas detector can be referred to as "normal mode". The gas detector can determine the concentration of the target gas in the external environment by using the deviation. For example, in some embodiments, the calibrated output reading may be obtained by subtracting the deviation from the detector signal of the gas detector indicating the concentration of the target gas in the external environment. In some embodiments, the deviation may be an average value obtained by averaging a plurality of detector signals of the gas detector. Then, the average value can be subtracted from the later detector signal to obtain the calibrated output reading. FIG. 4 illustrates an exemplary gas detector according to the present disclosure.

The photoelectric noise can be determined by the material of the electrodes and the intensity of the UV light from the UV lamp. In some embodiments, the gas detector may comprise a UV shielding cover provided close to one or two of the electrodes in the gas detector. When the UV lamp is turned ON, the UV shielding cover can reduce the ionization of the electrodes.

When the UV lamp is turned OFF, the target gas is possibly not ionized. At this moment, the detector signal of the gas detector can be referred to as the theoretical zero or absolute zero level of the concentration of the target gas. The fluctuation of the absolute zero level may only be affected by the system noise of the gas detector. If the gas detector can determine the accurate absolute zero level, then the output reading of the target gas can be more reliable and stable. The computed output reading may be based on the absolute zero level and the deviation.

When the UV lamp is turned ON, the UV light can irradiate the target gas and the electrodes in the ion chamber. The output signal of the gas detector at this moment comprises the photoelectric noise coming from the ionization of the electrodes and any existing target gas. In some embodiments, unwanted photoelectric noise may be reduced by adding a UV shielding cover (see, for example, FIG. 4). By incorporating the deviation as disclosed herein into the computation of the concentration of the target gas, other photoelectric noise caused by the ionization of the electrodes can be removed. When an ultra-low-concentration target gas (for example, a target gas with concentration less than 10 ppm, such as at a ppb concentration level) is detected, the photoelectric noise may be particularly harmful to the concentration of the target gas.

Figure 5:
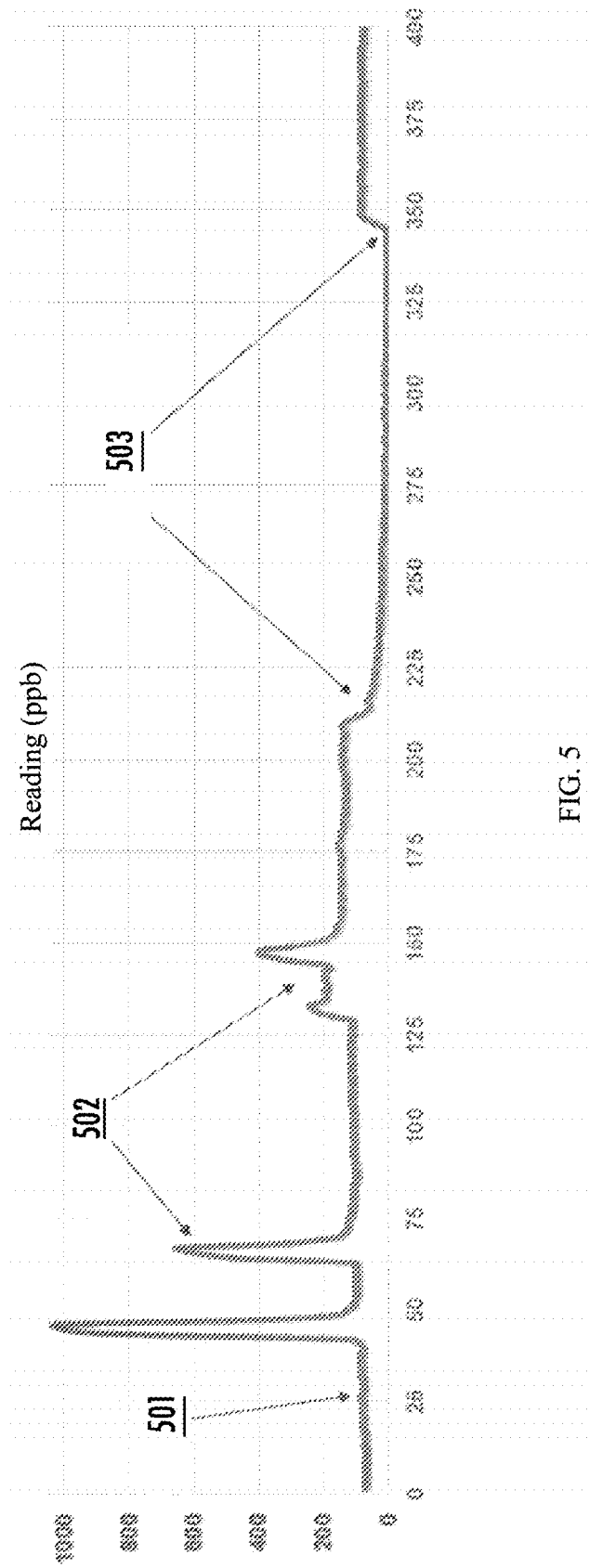
FIG. 5 illustrates readings from an exemplary gas detector according to one embodiment disclosed herein.
Figure 6:
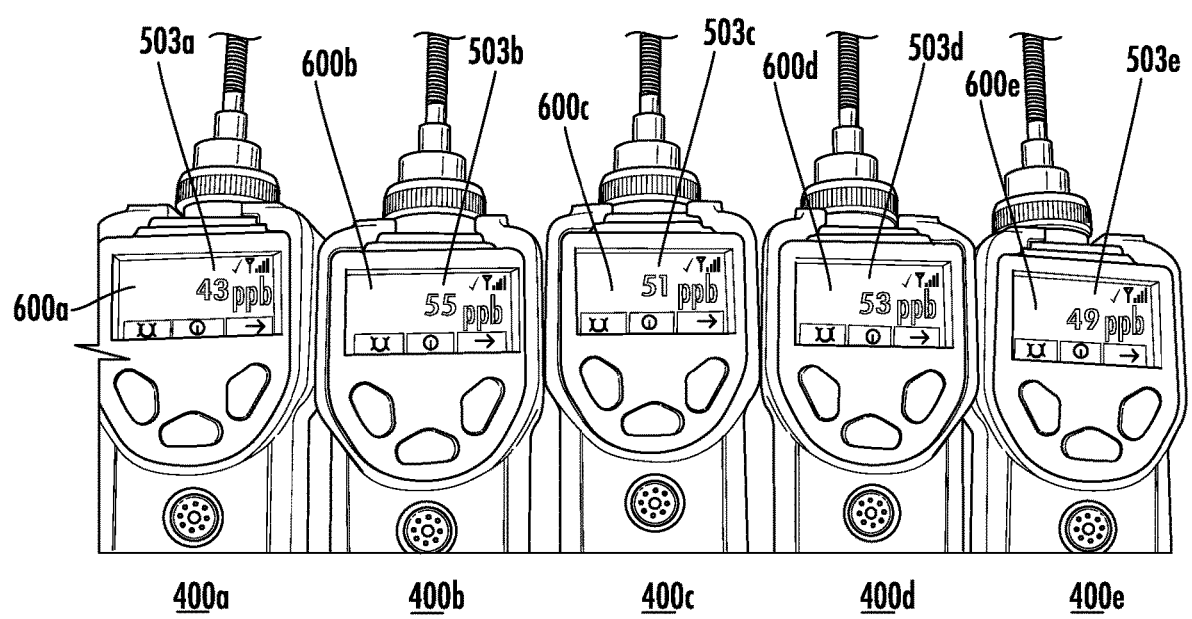
FIG. 6 illustrates readings from an exemplary gas detector according to one embodiment disclosed herein.

The gas detector and the method for calibrating the gas detector in the present invention provide an integrated solution to reduce the photoelectric noise coming from the output reading of the gas detector (such as a portable PID). Therefore, more accurate target gas readings can be obtained. The gas detector and the method for calibrating the gas detector in the present invention can provide more accurate readings than the existing gas detectors that use air calibration sensors. The gas detector and the method for calibrating the gas detector in the present invention can allow detecting the ultra-low-concentration target gas (for example, a target gas at a ppb concentration level). For example, the gas detector and the method for calibrating the gas detector in the present invention may allow the detecting target gases at concentration levels less than 10 ppm, such as a ppb concentration level (for example, less than 1 ppm), for example, less than 900 ppb, less than 800 ppb, less than 700 ppb, less than 600 ppb, less than 500 ppb or less than 400 ppb. Even at such low concentration levels, the gas detector and the method for calibrating the gas detector in the present invention can provide improved consistency of output readings improved stability compared with existing gas detectors. Exemplary gas detectors are illustrated in FIG. 5 and FIG. 6 as examples. The present disclosure may be incorporated the following into exemplary gas detectors, such as MinRAE 3000+, MiniRAE Lite+, ppbRAE 3000+, and UtraRAE 3000+.

In addition, the photoelectric noise of the electrodes for measuring the concentration of the target gas in the external environment can be determined. By using the same electrodes to determine the deviation and the measured output reading (or the detector signal in the normal mode), the calibrated output reading can be more accurate. The calibrated output reading is based on the electrode signal from the same electrodes for determining the deviation, and thus can more accurately reflect the photoelectric noise produced by the electrodes.

The gas detector in the present invention can be in any suitable form, such as in the form of a hand-held device, and can be positioned in a specific environment where the target gas may exist and be detected. For example, the gas detector may be installed separately from humans in part of the infrastructure and may be communicatively connected to a monitoring system. In some embodiments, the gas detector may be carried by a worker in a potentially hazardous working environment.

The target gas may comprise one or a plurality of gases, which are ideally detected by the gas detector. For example, the target gas may comprise benzene, toluene, gasoline, fuel oil, diesel fuel or other Volatile Organic Compounds (VOCs) that may cause harm to workers. The VOCs may include various solvents, fuels, degreasers, plastics, heat transfer fluids, lubricants, etc. The VOCs may be harmful to humans if inhaled and/or inhaled at concentrations exceeding a predetermined threshold. The VOCs may have a risk of explosion or fire, for example, when existing at concentrations exceeding a predetermined threshold. The gas detector and the method for calibrating the gas detector in the present invention can be used for monitoring industrial health and safety, environmental pollution and repair, hazardous substance treatment, ammonia detection, and refinery environments. For example, the gas detector may be used in refineries, chemical plants, manufacturing plants, or other environments where some gases need to be detected. In some embodiments, the target gas may not be particularly harmful or dangerous. In some embodiments, the target gas may be various types of gases, including oxygen and toxic gases such as carbon monoxide, sulfur dioxide and hydrogen sulfide. One or a plurality of gas detectors, such as a plurality of gas detectors, may be used in combination, each adjusted to detect a certain target gas or the same target gas. The gas detectors may be adjusted to detect certain target gases based on the main wavelengths of the UV lamps of the corresponding gas detectors.

Reference is made to the photoionization detector (PID) throughout the application. However, the present disclosure may be applied to various gas detectors to calibrate the detectors and ensure more accurate and reliable target gas readings. The system, method, and device in the present disclosure can be used in various applications. For example, the gas detector may be a photoionization detector (PID), an infrared detector, a laser gas detector, and other gas detectors. For example, when an infrared radiation (IR) source is turned ON, or when a laser is turned ON and a target gas is prevented from flowing through the IR detector or laser gas detector, the deviation may be determined in the IR detector or laser gas detector. Then, when the detector is open to the target gas, the deviation may be used to determine the concentration of the target gas.

The system, method and device can be used to calibrate the gas detector without obviously interfering with the normal operation of the sensor. The gas detector may be calibrated hourly, daily, weekly, monthly, etc.; may be calibrated after a predetermined period of time; may be calibrated as needed; may be calibrated in response to specified events or actions (for example, when a target gas concentration threshold is reached, when the gas detector moves to another position, etc.); or may be calibrated according to a combination thereof. For example, the deviation and/or absolute zero level may be determined after a predetermined period of time, as needed, in response to a specified event or action, or according to a combination thereof. The calibration of the gas detector may be performed, for example, within less than about 10 minutes, less than about 5 minutes, about 1 minute, or shorter durations. In some embodiments, the deviation may be determined within about 1 minute.

The electrodes may be added to a substrate (such as a flexible tape, T-I or a combination thereof) by means of screen printing and automatic puddling. Various selective deposition technologies, such as direct puddling, screen printing, or puddling on temporary supports may be used, followed by pressure transfer. Conductors may be used to electrically connect each electrode or several electrodes to a circuit 200. The electrodes may be made of the same material or different materials. In some embodiments, the electrodes may be made of one or a plurality of materials, such as platinum, iridium, ruthenium, gold, silver, carbon, or a combination thereof. For example, a catalyst material may comprise platinum, iridium, ruthenium, gold, silver, carbon or a mixture thereof, and may be used for the electrodes. The material and structure of the electrodes may be varied based on the expected application of the gas detector.

The gas detector may be used to detect a single target gas and two or more target gases. The gas detector may also monitor the temperature, pressure, position and movement of the gas detector and the environment where the gas detector is located (for example, "external environment"). This kind of measurement may be referred to as telemetry. In some embodiments, the measured temperature, pressure, position, and movement of the gas detector, as well as the external environment, may be used to initiate or modify gas detector calibration. For example, the gas detector may measure the temperature of the external environment and, based on the temperature, adjust the calibrated output reading of the target gas.

The method, device, system and computer program product in the present disclosure may be implemented by any one of the various devices. For example, the method, device, system, and computer program product in the exemplary embodiments may be implemented by a networking device (for example, enterprise platform, such as server or other network entities) configured to communicate with one or a plurality of devices (for example, gas detectors and monitoring stations such as control stations, etc.). Additionally or alternatively, the system may comprise a fixed computing device, such as a personal computer or a computer workstation. Further, the exemplary embodiments may be implemented by any one of various mobile devices, such as Portable Digital Assistants (PDAs), mobile phones, smart phones, laptops, tablets, wearable devices, or any combination thereof.

In some embodiments, the circuit 200 and/or gas detector system 100 described herein may be implemented in a single independent portable or fixed gas detector. For example, in some embodiments, all functions and processes described herein may be incorporated into the gas detector itself as an intelligent sensor module that provides fully processed digital output readings to instruments (for example, when ASICs and embedded processors are powerful enough). For example, the gas detector may comprise a microcontroller, an Application Specific Integrated Circuit (ASIC), a Programmable Logic Device (PLD), a Field Programmable Gate Array (FPGA), or some other logic processors.

FIG. 1 illustrates a gas detector system 100 including exemplary network architecture for the system. The system may comprise one or a plurality of devices and subsystems configured to implement some of the embodiments discussed herein. For example, the gas detector system 100 may comprise gas detectors 400A-400N, a server 140 and/or a client device 130, and may comprise, in addition to other devices (not shown), circuits, servers, databases, or the like disclosed in FIG. 2 to FIG. 3B, for example. The server 140 and/or client device 130 may comprise any suitable network server and/or other types of computing devices. In some embodiments, the server 140 and/or client device 130 may receive, determine, and transmit alarms, data, and instructions to the gas detectors 400A-400N by using data from a calibration database 300. The calibration database 300 (for example, illustrated in FIG. 3A and FIG. 3B) may be implemented as a data storage device, such as one or a plurality of Network Attached Storage (NAS) devices, or implemented as one or a plurality of separate database servers. The calibration database 300 comprises information accessed and stored by the gas detectors 400A-400N, the server 140 and/or the client device 130, so as to facilitate the operation of the gas detector system 100. For example, the calibration database 300 may comprise, but is not limited to, a plurality of telemetry data, application data, detected gas data, calibration data, gas detector data, and the like.

The server 140 and/or client device 130 may communicate with one or a plurality of gas detectors 400A-400N through a communication network 120. In this regard, the communication network 120 may comprise any wired or wireless communication network, including, for example, a wired or wireless Local Area Network (LAN), a Personal Area Network (PAN), a Metropolitan Area Network (MAN), a Wide Area Network (WAN) or the like, and any hardware, software and/or firmware (for example, a network router, etc.) required to implement the network. For example, the communication network 120 may comprise a cellular phone and 802.11, 802.16, 802.20, and/or WiMax networks. In addition, the communication network 120 may comprise a public network such as the Internet, a private network such as the intranet or a combination thereof, and may utilize various network protocols now available or later developed, including, but not limited to, TCP/IP based network protocols. For example, network protocols may be customized for adapting to calibration system needs.

The server 140 and/or client device 130 may receive electronic data from various sources (including, but not necessarily limited to, gas detector 400A-400N). For example, the server 140 and/or client device 130 may operate to receive or transmit telemetry data provided by the gas detectors 400A-400N, application data, detected gas data, calibration data, gas detector data, and the like.

The gas detectors 400A-400N, server 140, and/or client device 130 may be implemented by using a personal computer and/or other networking devices (such as cellular phones, tablets, mobile devices, and inventory management terminals), which may be used for any suitable purpose in addition to monitoring gases and/or gas detectors. "N" devices illustrated in FIG. 1 are only used for the purpose of description. The gas detector system 100 may comprise any number of gas detectors. In one embodiment, the gas detectors 400A-400N may be configured to view, create, and/or use other manners to interact with telemetry data, application data, detected gas data, calibration data, and/or gas detector data of the gas detectors, the system and/or the external environment where the gas detectors are located. The gas detectors, the system and/or the external environment where the gas detectors are located may be provided by the client device 130, server 140, gas detectors 400A-400N or other devices in the gas detector system 100. According to some embodiments, the server 140 and/or client device 130 may be configured to display telemetry data, application data, detected gas data, calibration data, and gas detector data on a display of the server 140 and/or client device 130, so as to view, create, edit and/or use other manners to interact with data. In some embodiments, the interface of the gas detectors 400A-400N may be different from the interface of the server 140 and/or client device 130. In addition to or in place of the server 140 and/or client device 130, the gas detectors 400A-400N may also be used. In addition to the devices, the gas detector system 100 may also comprise additional client devices and/or servers, etc. Additionally or alternatively, the gas detectors 400A-400N may interact with the gas detector system 100 through a web browser. As another example, the gas detectors 400A-400N may comprise various hardware or firmware designed to interact with the gas detector system 100.

In some embodiments, the gas detectors 400A-400N are photoionization detectors (PIDs). In some embodiments, the gas detectors 400A-400N may comprise any computing devices defined above. Electronic data received by the server 140 and/or client device 130 from the gas detectors 400A-400N may be provided in various forms and by adopting various methods. In some embodiments, the gas detectors 400A-400N, server 140 and client device 130 may comprise mobile devices, wearable devices, and the like.

In embodiments in which the gas detectors 400A-400N, client device 130 and/or server 140 are mobile devices (such as smart phones or tablets), the gas detectors 400A-400N, server 140 and/or client device 130 may execute "applications" (apps) to interact with the gas detector system 100. Such apps are usually designed to be executed on mobile devices (such as tablets or smart phones). For example, apps that are executed on mobile devices with operating systems, such as iOS®, Android®, or Windows® may be provided. These platforms often provide architecture that allows apps to communicate with each other and with specific hardware and software components of mobile devices. For example, the above-mentioned mobile operating systems respectively provide architecture for interacting with location service circuits, wired and wireless network interfaces, user contacts, and other applications. Communication with hardware and software modules executed outside apps is usually implemented through an Application Programming Interface (API) provided by the operating systems of the mobile devices.

In some embodiments of the exemplary gas detector system 100, information may be transmitted from the gas detectors 400A-400N to the server 140 and/or client device 130. In various embodiments, information may be transmitted directly by the gas detectors 400A-400N to the gas detector system 100 through the communication network 120, and the information may be transmitted to the gas detector system 100 through an intermediate device such as another client device or server. For example, the gas detectors 400A-400N may communicate with a desktop, a laptop, a tablet, a smart phone, or the like which is executing a client application program to interact with the gas detector system 100. In one embodiment, the information may comprise data such as telemetry data, application data, detected gas data, calibration data and gas detector data.

As described further below, the gas detector system 100 may comprise at least one server 140 and/or client device 130, which can create storage data entries based on the received information, so as to realize indexing and storage in the calibration database 300. In one embodiment, the storage data entries may comprise data such as telemetry data, application data, detected gas data, calibration data, and gas detector data.

In one embodiment, telemetry data, application data, detected gas data, calibration data, gas detector data, and the like may be parsed (for example, by using a PHP command) to determine information regarding gas detectors, especially with regards to electrodes, lamps, lamp drivers, UV shielding covers, UV windows, electrode plates, detected gases, external environment where the gas detectors are located, and etc.

Figure 2:
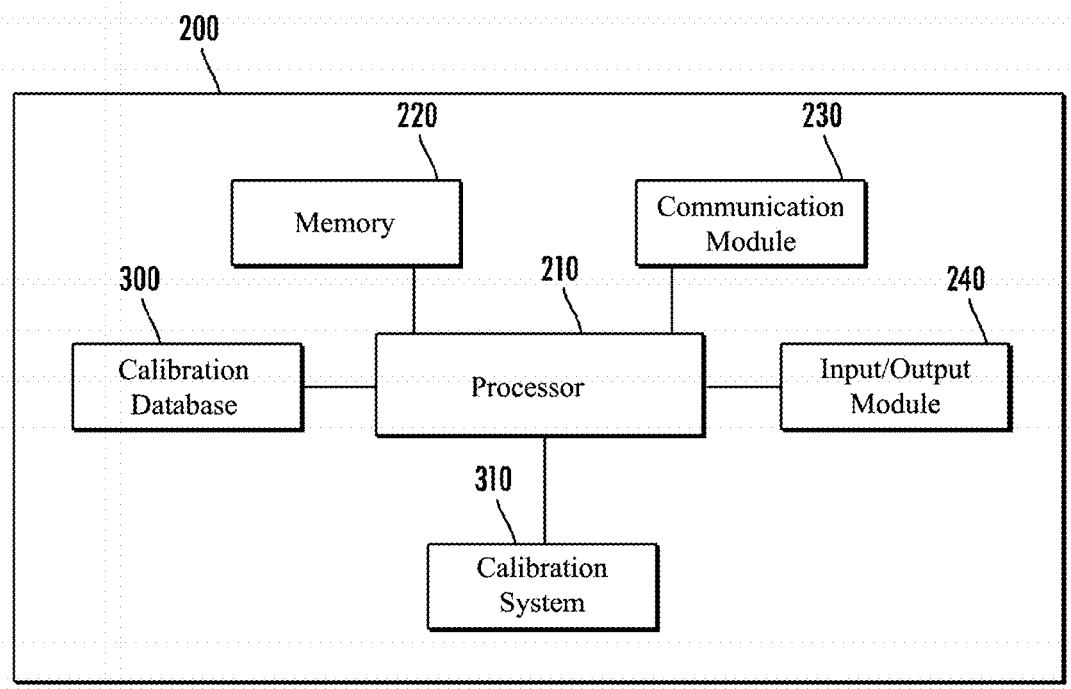
FIG. 2 illustrates a schematic diagram of a circuit that can be included in a device according to some embodiments discussed herein.
Figure 3A:
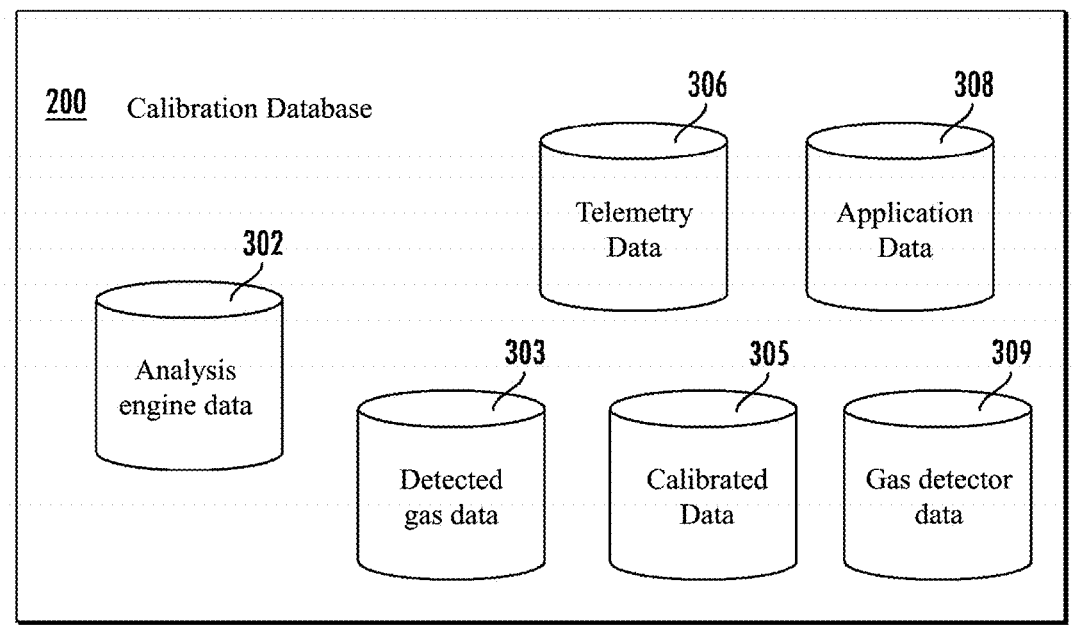
FIG. 3A illustrates an exemplary calibration database according to some embodiments discussed herein.

FIG. 2 illustrates a schematic block diagram of the circuit 200, some or all of which may be included in, for example, the server 140, the client device 130 and/or the gas detectors 400A-400N. Any one of the server 140, the client device 130, and/or the gas detectors 400A-400N may comprise one or a plurality of components of the circuit 200, and may be configured to execute the functions of the circuit 200 described herein independently or jointly with other devices in the communication network 120. As illustrated in FIG. 2, according to some exemplary embodiments, the circuit 200 may comprise various devices, such as a processor 210, a memory 220, a communication module 230, and/or an input/output module 240. In some embodiments, the calibration database 300 may also be included or alternatively included. As mentioned herein, "module" includes hardware, software, and/or firmware configured to execute one or a plurality of specific functions. In this regard, the devices of the circuit 200 as described herein may be implemented as, for example, circuits, hardware elements (for example, properly programmed processors, combinational logic circuits, etc.), and computer program products comprising computer-readable program instructions stored on a non-temporary computer-readable medium (for example, the memory 220). The computer-readable program instructions may be executed by appropriately configured processing devices (for example, the processor 210) or a certain combination thereof.

The processor 210 may be implemented as, for example, various devices comprising one or a plurality of microprocessors with accompanying digital signal processors; one or a plurality of processors without accompanying digital signal processors; one or a plurality of coprocessors; one or a plurality of multi-core processors; one or a plurality of controllers; processing circuits; one or a plurality of computers; and various other processing elements (including integrated circuits, such as ASICs or FPGAs, or a certain combination thereof). Therefore, although illustrated as a single processor in FIG. 2, in some embodiments, the processor 210 may comprise a plurality of processors. The plurality of processors may be implemented on the single server 140, the client device 130 and/or the gas detectors 400A-400N, or may be distributed on a plurality of such devices that are jointly configured to act as the circuit 200. The plurality of processors may operatively communicate with each other, and may be jointly configured to execute one or a plurality of functions of the circuit 200 as described herein. In one exemplary embodiment, the processor 210 is configured to execute instructions stored in the memory 220 or otherwise accessible by the processor 210. When executed by the processor 210, these instructions may enable the circuit 200 to execute one or a plurality of the functions of the circuit 200 as described herein.

No matter whether it is configured by hardware, firmware/software methods, or a combination thereof, the processor 210 may comprise entities capable of executing operations according to the embodiments of the present invention when correspondingly configured. Therefore, for example, when the processor 210 is implemented as an ASIC, an FPGA, or the like, the processor 210 may comprise specially configured hardware for implementing one or a plurality of operations described herein. Alternatively, as another example, when the processor 210 is implemented as an actuator of instructions (such as those that may be stored in the memory 220), the instructions may specifically configure the processor 210 to execute one or a plurality of algorithms and operations described herein, such as those discussed with reference to FIG. 12.

The memory 220 may comprise, for example, a volatile memory, a non-volatile memory, or a certain combination thereof. Although illustrated as a single memory in FIG. 2, the memory 220 may comprise a plurality of memory components. The plurality of memory components may be implemented on the single server 140, the client device 130, and/or the gas detectors 400A-400N, or may be distributed on a plurality of such devices. In various embodiments, the memory 220 may comprise, for example, a hard disk drive, a random access memory, a cache memory, a flash memory, a Compact Disc Read-Only Memory (CD-ROM), a Digital Versatile Disk Read-Only Memory (DVD-ROM), an optical disk, a circuit configured to store information, or a certain combination thereof. The memory 220 may be configured to store information, data (including data discussed with respect to the calibration database 300), application programs, instructions, and etc., so that the circuit 200 can execute various functions according to the embodiment of the present disclosure. For example, in at least some embodiments, the memory 220 is configured to cache input data for processing by the processor 210. Additionally or alternatively, in at least some embodiments, the memory 220 is configured to store program instructions for execution by the processor 210. The memory 220 may store information in the form of static and/or dynamic information. When the functions are executed, the stored information may be stored and/or used by the circuit 200.

The communication module 230 may be implemented as any apparatus or device included in a circuit, hardware, a computer program product or a combination thereof, which is configured to receive and/or transmit data from/to another device and/or network (such as a second circuit 200), and the like. The computer program product comprises computer-readable program instructions stored on a computer-readable medium (for example, the memory 220) and executed by a processing device (for example, the processor 210). In some embodiments, the communication module 230 (as with other components discussed herein) may be at least partially implemented as the processor 210 or otherwise controlled by the processor 210. In this regard, the communication module 230 may communicate with the processor 210, for example, through a bus. The communication module 230 may comprise, for example, antennas, transmitters, receivers, transceivers, network interface cards and/or supporting hardware and/or firmware/software, and is used for establishing communication with another device of the gas detector system 100. The communication module 230 may be configured to receive and/or transmit any data that may be stored by the memory 220 by using any protocol that can be used for communication between devices of the gas detector system 100. The communication module 230 may additionally or alternatively communicate with the memory 220, the input/output module 240 and/or any other component of the circuit 200, for example, through a bus.

In some embodiments, the circuit 200 may comprise an input/output module 240. The input/output module 240 may communicate with the processor 210 to receive instructions input by the user and/or to provide audible, visual, mechanical or other outputs to the user. Therefore, the input/output module 240 may comprise supporting devices, such as a keyboard, a mouse, a joystick, a display, a touch screen display, a microphone, a speaker, an RFID reader, a bar code reader, a biometric scanner, and/or other input/output mechanisms. In the embodiment in which the circuit 200 is implemented as a server or a database, compared with the embodiment in which the circuit 200 is implemented as an end-user machine or other types of devices designed for complex user interaction, various aspects of the input/output module 240 may be reduced. In some embodiments (as with other components discussed herein), the input/output module 240 may even be removed from the circuit 200. Alternatively, at least some aspects of the input/output module 240 may be implemented on a device used by the user to communicate with the circuit 200, for example, in the embodiment in which the circuit 200 is implemented as a server or a database. The input/output module 240 may communicate with the memory 220, the communication module 230 and/or any other component, for example, through a bus. One or a plurality of input/output modules and/or other components may be included in the circuit 200.

The calibration database 300 and a calibration system 310 may be additionally or alternatively included and configured to execute the functions discussed herein with respect to analyzing, storing, generating, and/or editing data. In some embodiments, some or all of the functions of analyzing, storing, generating, and/or editing data may be executed by the processor 210. In this regard, the exemplary processes and algorithms discussed herein may be executed by at least one processor 210, the calibration database 300 and/or the calibration system 310. For example, a non-temporary computer-readable medium may be configured to store firmware, one or a plurality of application programs, and/or other software. The firmware, one or a plurality of application programs, and/or other software comprise instructions that can be executed to control each processor (for example, the processor 210, the calibration database 300 and the calibration system 310) of the components of the circuit, thereby implementing various operations and other computer-readable program code parts, including the examples described above. Therefore, a series of computer-readable program code parts are implemented in one or a plurality of computer program products, and can be used together with computing devices, servers and/or other programmable devices to produce a machine-implemented process.

In some embodiments, the calibration database 300 may be provided, comprising telemetry data 306, application data 308, detected gas data 303, calibration data 305, gas detector data 309 and/or analysis engine data 302. The telemetry data 306 may comprise various information, such as measured values of temperature, pressure, movement, position, etc., which may be measured periodically, after a predetermined period of time, after a specified event occurs, or as needed. The application data 308 may comprise various information specific to applications using the gas detectors 400A-400N, such as typical or expected telemetry data, position data, or other data related to applications using the gas detectors 400A-400N. The detected gas data 303 may comprise various information, such as the type of the target gas, the historical output readings thereof, and other data related to the target gas. The calibration data 305 may comprise various information, such as calibration frequency (for example, time interval between calibrations); calibration length (for example, duration of calibration); historical calibration information; start of calibration (for example, action to start calibration); historical absolute zero level; historical deviation; and any other information about calibration of the gas detectors 400A-400N. The gas detector data 309 may comprise various types of information, such as the manufacture/model/serial number of the detectors; the type of the detectors; the expected service life of the detectors; the first use date of the detectors; the maintenance history of the detectors; the expected date of the maintenance of the detectors; the relative positions of the detectors in the environment; the limit of the reading of the gas detectors; the type of the electrodes/UV lamps/UV shielding covers/other components in the detectors; the expected service life of the electrodes/UV lamps/UV shielding covers/other components in the detectors; the first use date of the electrodes/UV lamps/UV shielding covers/other components in the detectors; and any other information regarding the gas detectors 400A-400N and the use thereof. Additionally or alternatively, the calibration database 300 may comprise an analysis engine data 302, providing any additional information required by the processor 210 to store, analyze, generate, and edit data.

The calibration system 310 may be configured to analyze groups of data, such as data in the calibration database 300. In this way, the calibration system 310 may support a variety of algorithms, including those discussed below with respect to the telemetry data 306, application data 308, detected gas data 303, calibration data 305, gas detector data 309, and/or analysis engine data 302, so that the selected algorithm can be selected during operation. In addition, the configuration of the present invention can achieve flexibility in the aspect of configuring the additional background.

Figure 3B:
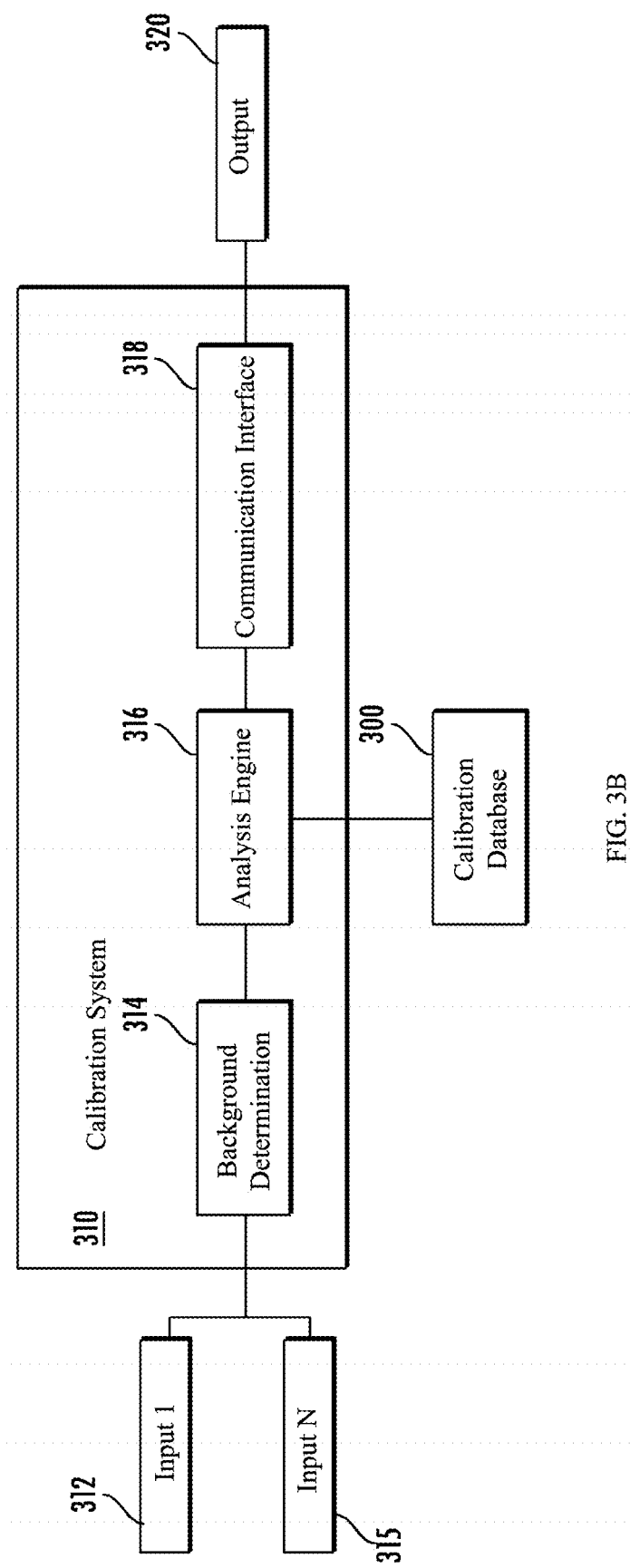
FIG. 3B illustrates an exemplary calibration system according to some embodiments discussed herein.

In some embodiments, referring to FIG. 3B, the calibration system 310 may comprise a background determination module 314, an analysis engine 316, and a communication interface 318, all of which may communicate with the calibration database 300. The calibration system 310 may receive one or a plurality of signals (for example, detector signals, electrode signals, query signals, response signals, instructions, output readings, absolute zero level, deviations, and etc.) that may contain information such as the telemetry data 306, application data 308, detected gas data 303, calibration data 305, gas detector data 309 and/or analysis engine data 302. The calibration system 310 may generate appropriate signals or outputs, as responses, that may contain information such as the telemetry data 306, application data 308, detected gas data 303, calibration data 305, gas detector data 309, and/or analysis engine data 302. The calibration system 310 may use any algorithm or process disclosed herein to receive one or a plurality of signals (for example, detector signals, electrode signals, query signals, response signals, instructions, output readings, absolute zero levels, deviations, etc.) that may contain information such as the telemetry data 306, application data 308, detected gas data 303, calibration data 305, gas detector data 309 and/or analysis engine data 302. The calibration system 310 may generate appropriate signals or outputs, as responses, that may contain information such as the telemetry data 306, application data 308, detected gas data 303, calibration data 305, gas detector data 309 and/or analysis engine data 302. In some other embodiments, for example, when the circuit 200 is implemented in the server 140, client device 130, and/or gas detectors 400A-400N, the calibration system 310 may be located in another circuit 200 or another device, for example, another server 140, another client device 130, gas detector 400A-400N, and/or other client devices.

The calibration system 310 may be configured to access data corresponding to a plurality of signals (for example, detector signals, electrode signals, query signals, response signals, instructions, output readings, absolute zero levels, deviations, etc.) that may contain information such as the telemetry data 306, application data 308, detected gas data 303, calibration data 305, gas detector data 309 and/or analysis engine data 302. The calibration system 310 may generate appropriate signals or outputs, as responses, that may contain information such as the telemetry data 306, application data 308, detected gas data 303, calibration data 305, gas detector data 309, and/or analysis engine data 302.

The system may receive a plurality of inputs 312, 315 from the circuit 200 and process the inputs in the calibration system 310 to generate an output 320. The output 320 may comprise s signals or outputs containing appropriate information as responses. In some embodiments, the calibration system 310 may execute background determination by using the background determination module 314, process data in the analysis engine 316, and output results through the communication interface 318. In each of these steps, data can be extracted from a plurality of sources, including the calibration database 300.

When the inputs 312, 315 are received by the calibration system 310, background determination may be performed by using the background determination module 314. What is determined in background determination comprises information such as telemetry data 306, application data 308, detected gas data 303, calibration data 305, gas detector data 309 and/or analysis engine data 302, which indicate, for example, which received input is initiated by the gas detectors 400A-400N, the type of input provided (for example, the received are detector signals, electrode signals, query signals, response signals, instructions, output readings, absolute zero levels, deviations, etc.), and cases where the received input is initiated (for example, the positions that the gas detectors 400A-400N are located, the time that the input is received, the signal or information received before input, and etc.). The information may provide a background to the analysis of the calibration system 310 so as to determine the output. For example, the background determination module 314 may notify the calibration system 310 of the signal and/or information to be outputted.

Then, the calibration system 310 can compute the output by using the analysis engine 316. The analysis engine 316 extracts information about the applicable signal, the gas detectors 400A-400N, and the like from the calibration database 300, and then computes the output according to the background determined by the background determination module 314. The output changes based on the input. Then, the communication interface 318 outputs the output 320 to the circuit 200 for storage, displays on appropriate interfaces, transmits to other devices or servers, or uses other manners to perform subsequent actions. For example, the background determination module 314 may determine that a detector signal, a query signal, a response signal, an instruction, an output reading, an absolute zero level, a deviation, or the like is received. Based on the information and applicable telemetry data 306, application data 308, detected gas data 303, calibration data 305, gas detector data 309, and/or analysis engine data 302, the analysis engine 316 can determine appropriate outputs, such as an alarm indicating that the concentration of the target gas in the environment of the gas detectors 400A-400N related to the target gas signal reaches a threshold. The analysis engine 316 can receive instructions to calibrate the gas detectors 400A-400N. Based on the information and applicable telemetry data 306, application data 308, detected gas data 303, calibration data 305, gas detector data 309 and/or analysis engine data 302, the analysis engine 316 can determine that the gas detectors 400A-400N should be switched from the second mode of the UV lamp to the first mode, and the target gas should be prevented from flowing to the gas detectors 400A-400N. Then, the gas detectors 400A-400N can measure the deviation based on the current generated at the electrodes. The deviation may be stored in the calibration database 300 for future use. Based on the applicable telemetry data 306, application data 308, detected gas data 303, calibration data 305, gas detector data 309 and/or analysis engine data 302, the analysis engine 316 can determine that a certain period of time has passed after previous calibration. Then, the circuit 200 can initiate the appropriate calibration of the gas detectors 400A-400N.

It should be understood that any such computer program instructions and/or other types of codes may be loaded onto a circuit of a computer, a processor, or other programmable device to produce a machine, so that the computer, the processor, or the other programmable circuit executing codes on the machine creates a device for implementing various functions (including those described herein).

It should also be noted that all or some of the information discussed herein may be based on data received, generated, and/or maintained by one or a plurality of components of a local or networked system and/or the circuit 200. In some embodiments, at least some of the functions discussed herein may also be provided with the aid of one or a plurality of external systems (such as remote cloud computing and/or data storage systems).

As described above and as can be understood based on the present disclosure, the embodiments of the present invention may be configured as methods, personal computers, servers, mobile devices, back-end network devices, or the like. Therefore, the embodiments may comprise various devices, including complete hardware or any combination of software and hardware. Further, the embodiments may be in the form of a computer program product on at least one non-temporary computer-readable storage medium. The computer-readable storage medium has computer-readable program instructions (for example, computer software) contained in the storage medium. Any suitable computer-readable storage medium may be used, including non-temporary hard disk, CD-ROM, flash memory, optical storage device or magnetic storage device.

The embodiments of the present invention have been described above with reference to block diagrams and flowcharts of the method, the device, the system, and the computer program product. It should be understood that each block of the circuit diagrams and the process flowcharts, and a combination of the blocks in the circuit diagrams and the process flowcharts can be respectively implemented by various devices including computer program instructions. These computer program instructions may be loaded onto a general-purpose computer, a special-purpose computer or other programmable data processing devices (such as the processor 210, the calibration database 300 and/or the calibration system 310 discussed above with reference to FIG. 2) to produce a machine, so that the computer program product comprises instructions for executing and creating devices for implementing functions specified in one or a plurality of flowcharts on a computer or other programmable data processing devices.

These computer program instructions may also be stored in a computer-readable storage device (for example, the memory 220). The computer-readable storage device may instruct a computer or other programmable data processing devices to operate in a particular way, so that the instructions stored in the computer-readable storage device produce a product including the computer-readable instructions for implementing the functions discussed herein. The computer program instructions may also be loaded onto a computer or other programmable data processing devices, to facilitate execution of a series of operation steps on the computer or other programmable devices to produce a process implemented by the computer, so that the instructions executed on the computer or other programmable devices provide steps for implementing the functions discussed herein.

Therefore, the blocks in the block diagrams and the flowcharts support a combination of devices for executing specified functions, a combination of steps for executing specified functions, and program instruction devices for executing specified functions. It should also be understood that each block of the circuit diagrams and the process flowcharts, as well as combination of the blocks in the circuit diagrams and the process flowcharts, may be implemented by dedicated hardware-based computer systems that execute specified functions or steps or by a combination of dedicated hardware and computer instructions.

FIG. 4 illustrates an exemplary gas detector according to one embodiment disclosed herein. In the embodiment illustrated in FIG. 4, a gas detector 400 comprises a switch 401, a UV lamp 406, a lamp driver 404, a UV window 410, an electrode plate 408, a UV shielding cover 412, a first electrode 414a, and a second electrode 414b. The switch 401 and the lamp driver 404 operate to turn ON (first mode) and turn OFF (second mode) the UV lamp 406. The gas detector 400 may comprise various mechanisms for operating the UV lamp 406 to move from the first mode to the second mode and return to the first mode. For example, in some embodiments, the calibration system 310 and/or the processor 210 may operate to switch the UV lamp 406 from the first mode to the second mode and return to the first mode.

The electrode plate 408 operates so as to irradiate UV lamp 406. In the embodiment illustrated in FIG. 4, the UV lamp 406 is associated with a UV window 410. UV light emitted from the UV lamp 406 passes through the UV window 410 before irradiating the positions near the first electrode 414a and the second electrode 414b. In some embodiments, the UV lamp 406 may be a vacuum ultraviolet (VUV) lamp.

The first electrode 414a and the second electrode 414b form a pair of electrically biased electrodes. The first electrode 414a and the second electrode 414b may comprise at least two parallel electrode plates that provide stable DC bias voltage.

The gas detector 400 comprises a gas inlet 403, wherein gases such as a target gas 416 may enter the gas detector 400 from the gas inlet 403. The target gas 416 is ionized by photons emitted from the UV lamp 406, thereby forming ions that accumulate on the first electrode 414a and the second electrode 414b. By including a calibration filter (see, for example, FIG. 9), injecting or pulling a calibration gas through the gas inlet 403, or using other manners to prevent the target gas from entering the gas inlet 403, the target gas can be prevented from entering the gas inlet 403. The calibration gas may comprise any suitable gas that is not ionized by the UV lamp 406 at the wavelength of the UV light emitted from the UV lamp 406. For example, the calibration gas may comprise nitrogen gas.

In the embodiment illustrated in FIG. 4, the gas detector 400 comprises a filter 434, the filter 434 comprises an amplifier 424, and the amplifier 424 enhances the amplitude of an electrode signal 422 based on reference voltage 428. The filter 434 comprises a resistor 432 and a capacitor 430. The filter 434 may be implemented in various ways in addition to the way illustrated in FIG. 4, and may comprise more than one resistor 432 and/or capacitor 430.

The filter 434 outputs the filtered electrode signal 426, which can be inputted to an analog-to-digital converter (not shown). Then, the analog-to-digital converter can output a detector signal to the calibration system 310, the processor 210 or other components of the circuit 200. The use of the filter 434 and the analog-to-digital converter may be considered for signal conditioning. Various modifications to the process may be used without departing from the spirit of the present disclosure, and some or all of the process may be executed by the calibration system 310, the processor 210, or other components of the circuit 200.

When the gas detector 400 is calibrated, the UV lamp 406 may be in the second mode to determine an absolute zero level. Then, the mode of the UV lamp 406 is changed to the first mode through the switch 401 and/or the lamp driver 404. A deviation can be determined by using the obtained electrode signal 422, filtered electrode signal 114, and/or detector signal. Then, the deviation may be used when the gas detector 400 is in a normal mode, i.e., the UV lamp 406 is in the first mode and the gas inlet 403 is open to the target gas. For example, in some embodiments, a calibrated output reading may be obtained by subtracting the deviation from the detector signal of the gas detector 400, which indicates the concentration of the target gas in an external environment. The detector signal of the gas detector 400 in the normal mode may be referred to as the measured output reading. In some embodiments, the deviation may be an average value obtained by averaging a plurality of detector signals of the gas detector 400. Then, the average value can be subtracted from the later detector signal or the measured output reading to obtain the calibrated output reading. The absolute zero level may also be subtracted from the detector signal of the gas detector 400 when the calibrated output reading is obtained. A plurality of detector signals may be averaged to determine the average absolute zero level, and then the average absolute zero level is used to obtain the calibrated output reading. Both the absolute zero level and the deviation may be updated periodically, as needed, in response to specified events and a combination thereof to maintain an accurate calibrated output reading. The absolute zero level may be updated when the deviation is updated or according to different time schedules. For example, the absolute zero level and the deviation may be determined at the first time, and then the absolute zero level may be updated more frequently than the deviation, or vice versa. For example, the absolute zero level may be updated every hour, whereas the deviation is updated at lower frequency or is not updated at all. It can be seen that the deviation is relatively constant, thus frequent updates may not be required.

The calibration of the gas detector 400 may be performed, for example, within less than about 10 minutes, less than about 5 minutes, about 1 minute, or shorter durations. In some embodiments, the deviation may be determined within about 1 minute.

FIG. 5 illustrates data recordings from the exemplary gas detector 400 according to one embodiment disclosed herein.

In particular, FIG. 5 illustrates more accurate calibrated output readings obtained by using this calibration. FIG. 5 illustrates environment air readings prior to the disclosed calibration 501, target gas readings prior to the disclosed calibration 502, and calibrated output readings after the calibration 503. As illustrated in FIG. 5, by using the disclosed calibration, unwanted photoelectric noise can be removed from the obtained readings, so as to obtain more accurate target gas readings.

FIG. 6 illustrates readings from the exemplary gas detector 400 according to one embodiment disclosed herein. In particular, FIG. 6 illustrates consistency throughout a plurality of gas detectors 400a-400e when the gas detector and the method for calibrating the gas detector according to the present invention are adopted. Each of the gas detectors 400a-400e has been calibrated according to the present disclosure. Then, each of the gas detectors 400a-400e is exposed to the same environment. Interfaces 600a-600e of the gas detectors 400a-400e display calibrated output readings 503a-503e of the target gas in the environment. As illustrated in FIG. 6, the gas detectors 400a-400e have similar computed readings 601a-601e of the target gas.

Figures 7A, 7B:
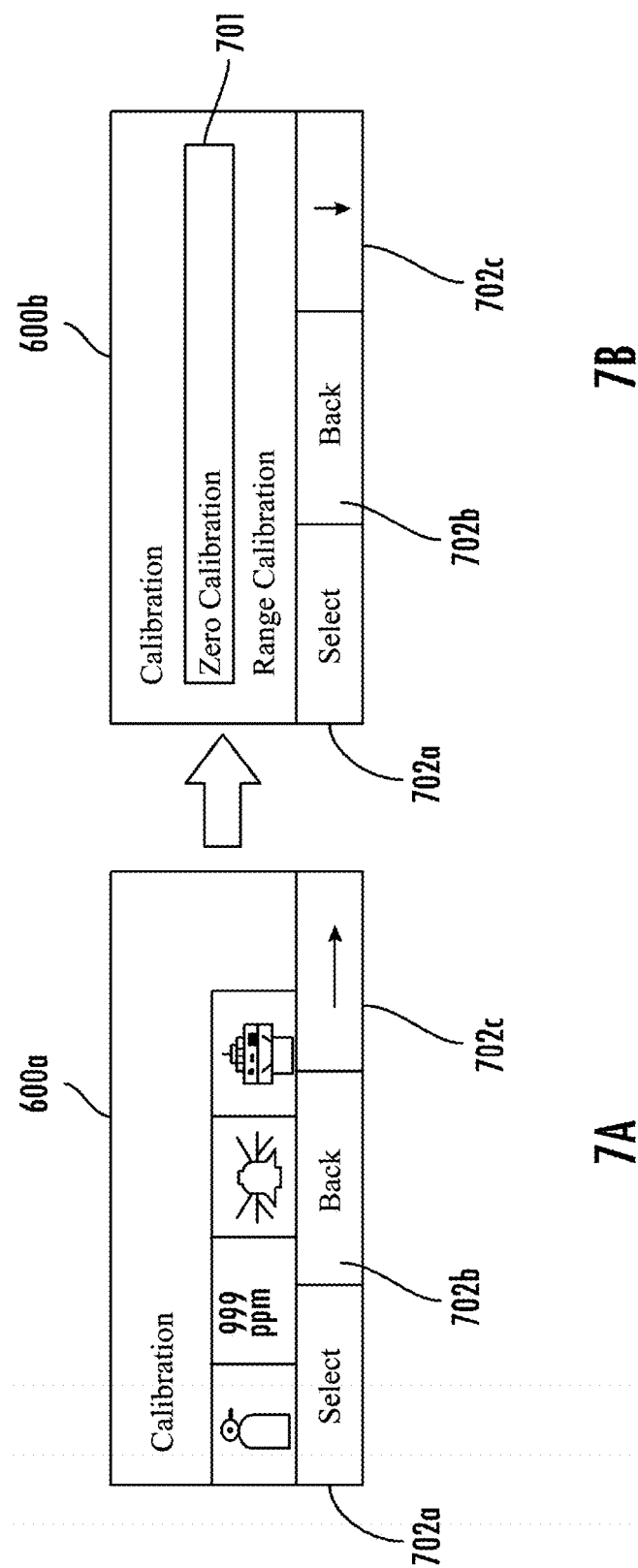
FIG. 7a and FIG. 7b illustrate an exemplary interface of a gas detector according to one embodiment disclosed herein.

FIG. 7a and FIG. 7b illustrate exemplary interfaces 600a, 600b of the gas detector 400 according to one embodiment disclosed herein. In particular, FIG. 7a and FIG. 7b illustrate operation menus displayed on the exemplary interfaces 600a, 600b of the gas detector 400 according to one embodiment disclosed herein. In the embodiment illustrated in FIG. 7a, the operation menu is used to calibrate the gas detector 400. When calibration is selected, the operation menu illustrated in FIG. 7b can be displayed. As illustrated in FIG. 7b, zero calibration 701 may be selected to start this method for calibrating the gas detector. Actuators 702a, 702b, 702c may be used on interfaces 600a, 600b to initiate desired actions, such as selecting zero calibration 701 of the gas detector 400. As described above, the gas detector 400 may comprise various input mechanisms, such as buttons, keys and levers, so as to initiate a desired action, which may include calibration of the gas detector 400. In some embodiments, the calibration of the gas detector 400 may be programmed to be performed periodically or after a certain event occurs (for example, when the calibrated output reading of the target gas is high or the calibrated output reading of the target gas is low). In some embodiments, the gas detector 400 may be programmed to be calibrated after preset years of use thereof or a predetermined period of use thereof. Without departing from the present disclosure, the gas detector may be programmed to initiate the calibration of the gas detector 400 through various mechanisms and at various points in the use of the gas detector 400.

Figure 8:
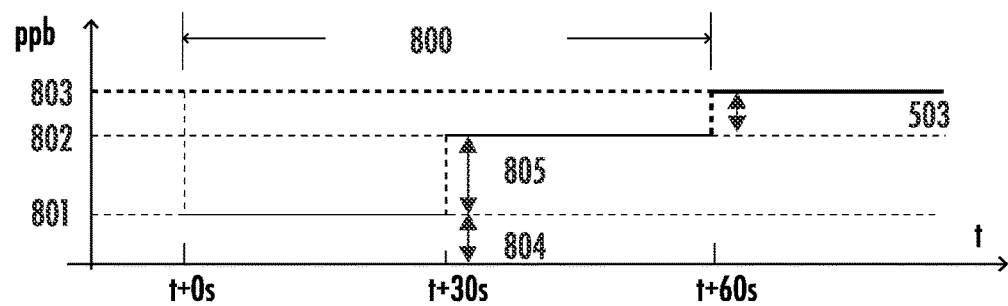
FIG. 8 illustrates zero calibration according to one embodiment disclosed herein.

FIG. 8 illustrates the calibration according to one embodiment disclosed herein. In the embodiment illustrated in FIG. 8, during calibration 800, the gas detector 400 enables the UV lamp 406 to be in the second mode to determine an absolute zero level 801 by turning OFF the UV lamp 406. The absolute zero level 801 may be associated with an average voltage value. The absolute zero level 801 represents electric noise 804. Then, the UV lamp 406 is turned ON so that it is in the first mode, and the average photoelectric noise 805 of UV light is determined when the target gas is not ionized at all. A deviation 802 is illustrated in FIG. 8. The photoelectric noise 805 may change based on the material of the first electrode 414a and the second electrode 414b and/or the intensity of UV light emitted from the UV lamp 406. Then, the target gas 416 can be allowed to enter the gas detector 400 and be ionized by the UV lamp 406. The gas detector 400 measures the concentration of the target gas 416 to obtain the measured output reading 803 in FIG. 8, and then, based on the deviation, computes the calibrated output reading 503 in FIG. 8. Therefore, the calibrated output reading 503 takes into account electric and photoelectric noises of the gas detector 400. Therefore, the obtained concentration of the target gas 416 in the external environment is more accurate.

After the calibration is completed, the gas detector 400 saves the deviation 802. After removal of any calibration tube, calibration gas or other mechanism that prevents the target gas 416 from flowing to the gas detector 400, the gas detector 400 can operate in the normal mode and obtain the true reading of the target gas 416 in the external environment. The deviation 802 can be subtracted from the measured output reading 803 to obtain the calibrated output reading 503, which may be the true reading of the concentration of the target gas. By averaging the deviation 802 over time or replacing the previous deviation 802 with the newly determined deviation 802, the deviation 802 can be updated over time (such as within or after a specific period of time). In some embodiments, the deviation 802 may change when the first electrode 414a and the second electrode 414b are changed or when the light intensity of the UV lamp 406 has changed (for example, if the UV light is contaminated with dust). Calibration may be performed at a fixed time such as periodically, or as needed, for example, when required by an operator. In some embodiments, the calibration may be executed in real time by using automatic zero calibration, so as to ensure that the true reading of the concentration of the target gas is more reliable.

Figure 9:
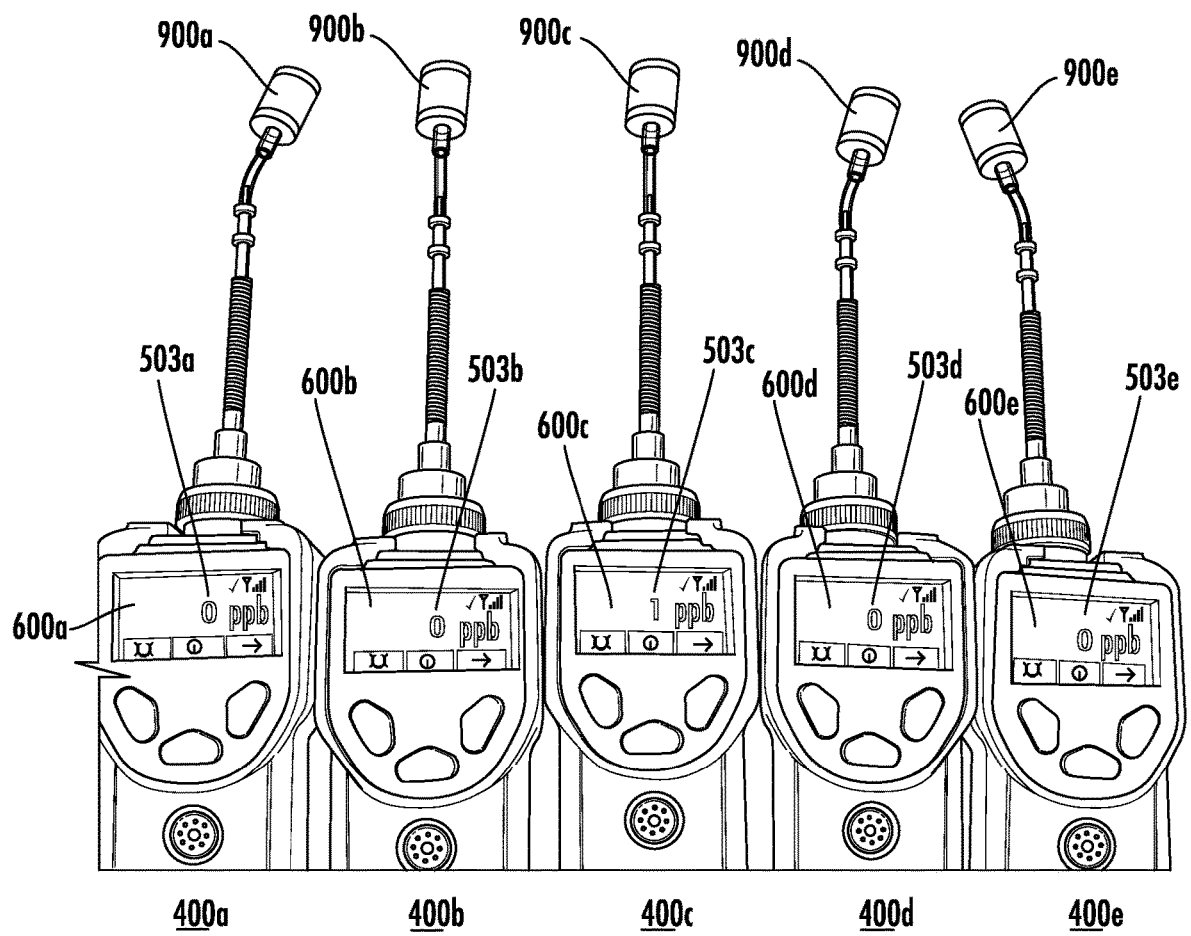
FIG. 9 illustrates readings from a plurality of gas detectors after calibration according to one embodiment disclosed herein.
Figure 10:
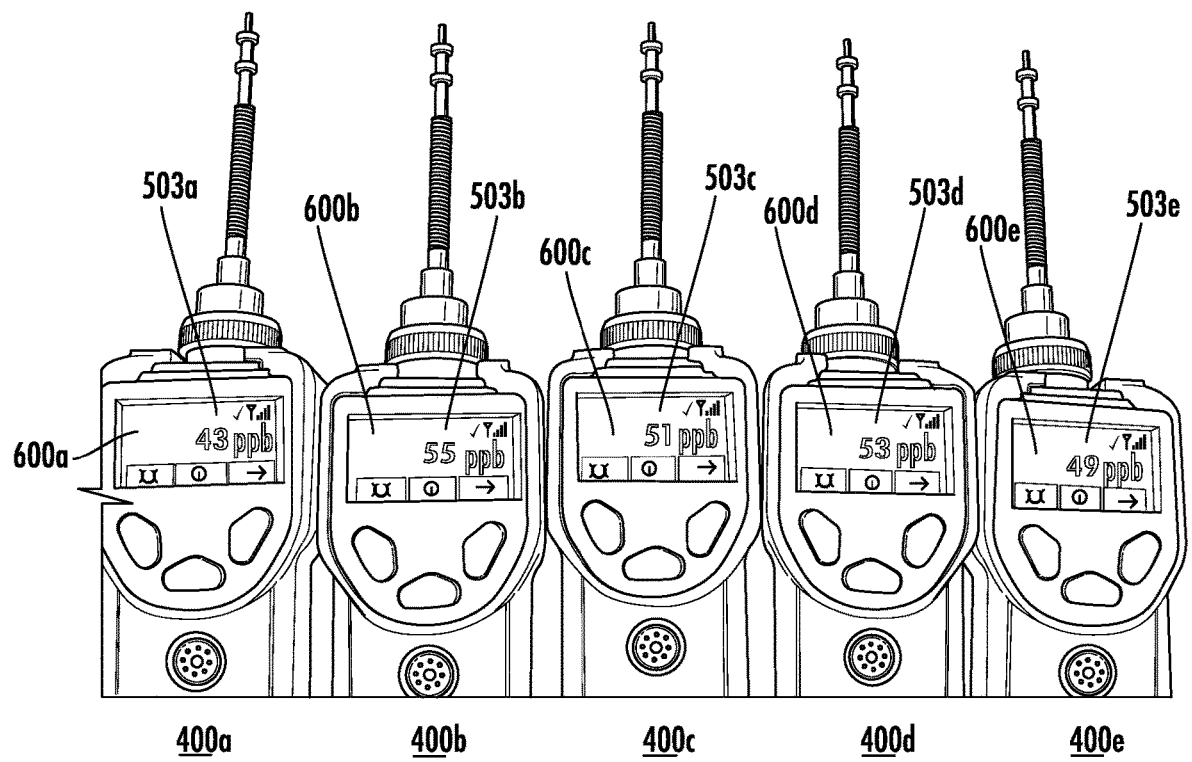
FIG. 10 illustrates readings from a plurality of gas detectors according to one embodiment disclosed herein.

FIG. 9 and FIG. 10 illustrate verification tests. For example, FIG. 9 illustrates readings from a plurality of gas detectors 400 after calibration according to one embodiment disclosed herein. In particular, FIG. 9 illustrates gas detectors 400a-400e with interfaces 600a-600e, wherein the interfaces 600a-600e display the calibrated output readings 503 during calibration 503a-503e. In the embodiment illustrated in FIG. 9, calibration filters 900a-900e are used to prevent the target gas from flowing to the gas detectors 400a-400e. FIG. 10 illustrates readings from a plurality of gas detectors 400 according to one embodiment disclosed herein. In particular, FIG. 10 illustrates gas detectors 400a-400e with interfaces 600a-600e, wherein the interfaces 600a-600e display the calibrated output readings 503a-503e of the target gas after calibration.

Figure 11:
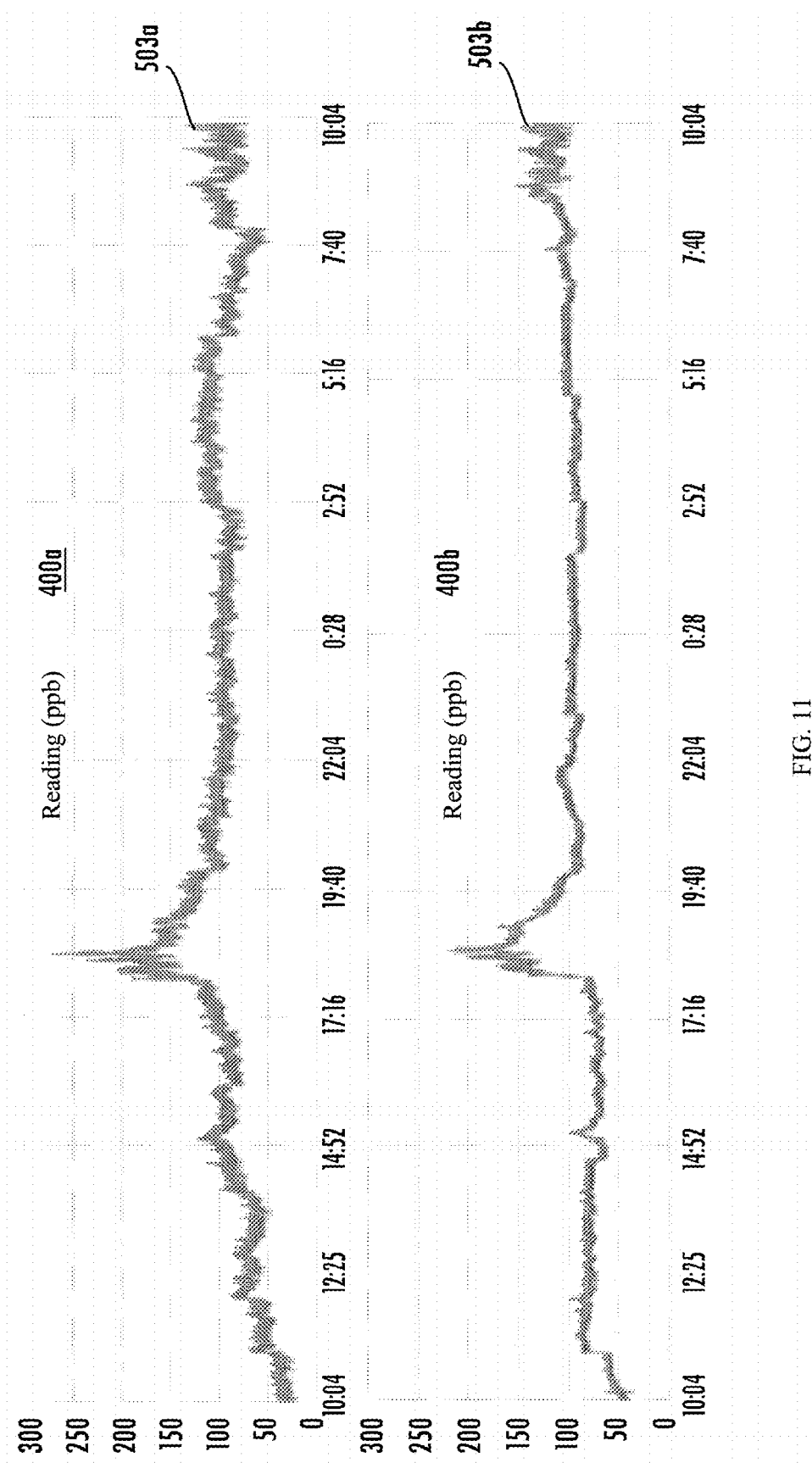
FIG. 11 illustrates readings from two gas detectors within 24 h according to one embodiment disclosed herein.

FIG. 11 illustrates data records of two gas detectors which continuously operate for 24 hours in the same office environment. In particular, FIG. 11 illustrates readings from two gas detectors 400a, 400b within 24 h according to one embodiment disclosed herein. As illustrated in FIG. 11, the detector signals of the two gas detectors are consistent during the 24 hours, which indicates the consistency of the deviation.

Figure 12:
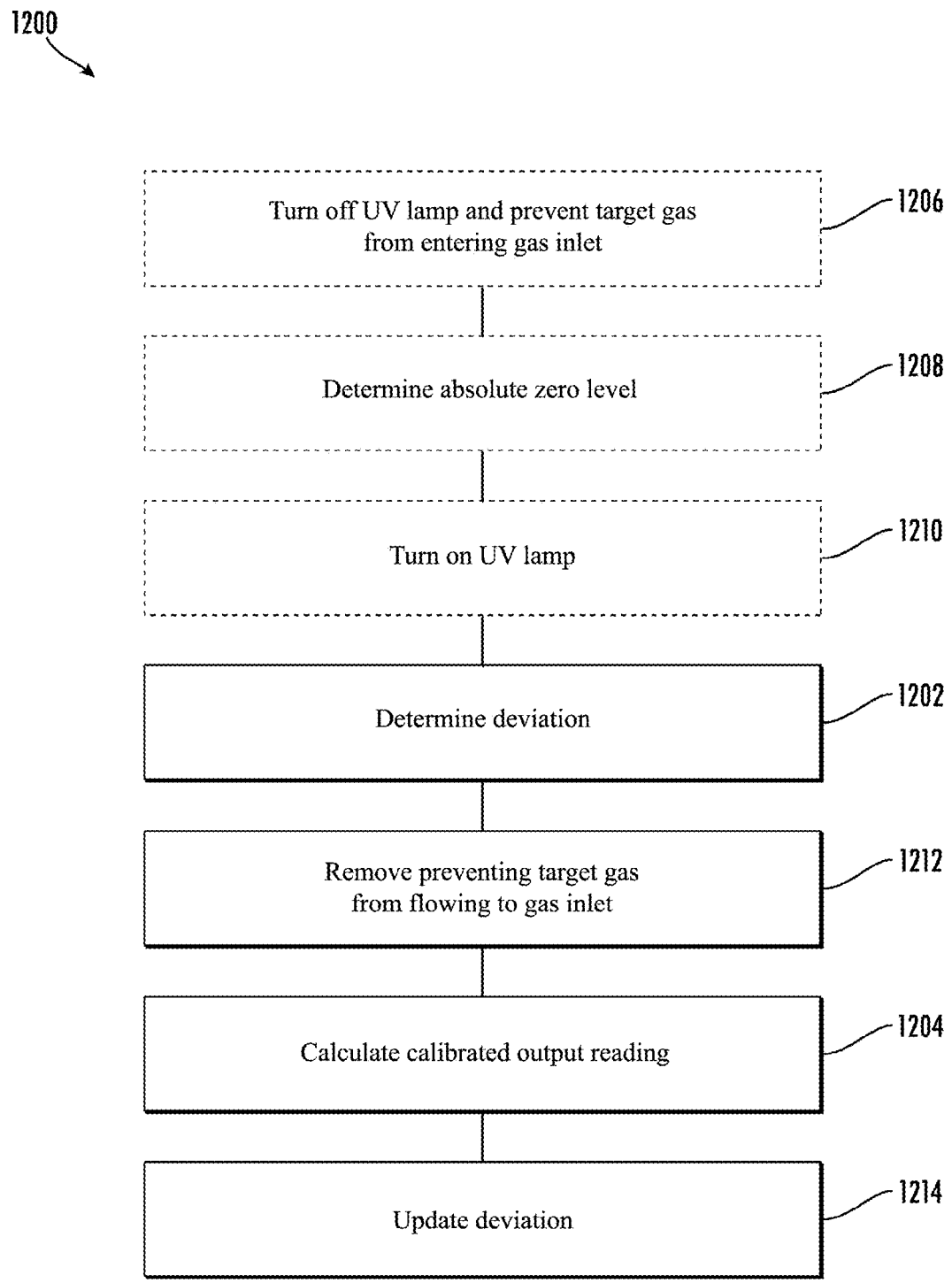
FIG. 12 illustrates a flowchart of exemplary operations according to one embodiment disclosed herein.

FIG. 12 illustrates a flowchart of exemplary operations according to one embodiment disclosed herein. In particular, FIG. 12 illustrates a method 1200, comprising, when a UV lamp of a gas detector is in a first mode and a target gas is prevented from entering a gas inlet of the gas detector, determining a derivation 1202; and when the gas inlet is open to the target gas, computing a calibrated output reading 1204 based on the deviation. As discussed above, the first mode of the UV lamp is an operating mode of the UV lamp so that UV light is emitted from the UV lamp. When the deviation 1202 is determined, the target gas may be prevented from entering the gas inlet by providing a calibration filter in the gas detector, inletting a calibration gas, or adopting a combination thereof. The method 1200 may comprise turning off the UV lamp and preventing the target gas from flowing to the gas inlet 1206, and then turning on the UV lamp 1210 before the step of determining the deviation 1202.

In some embodiments, the step of determining the deviation 1202 may be based on current generated by a pair of electrically biased electrodes of the gas detector when exposed to the UV light emitted from the UV lamp. The current may be generated by at least part of the pair of electrically biased electrodes which are ionized when exposed to the UV light emitted from the UV lamp. In some embodiments, the step of determining the deviation 1202 may comprise averaging a plurality of detector signals based on the current or electrode signals generated by the pair of electrically biased electrodes of the gas detector. In some embodiments, the step of determining the deviation 1202 may be executed after a predetermined period of time, after a specified event occurs, as needed or according to a combination thereof. In some embodiments, the method 1200 may further comprise updating the deviation 1214 after a predetermined period of time, after a specified event occurs, as needed or according to a combination thereof. The deviation may be updated by preventing the target gas from flowing to the gas inlet and obtaining the detector signals based on the current generated by the pair of electrically biased electrodes of the gas detector.

In some embodiments, the method 1200 may further comprise determining an absolute zero level when the UV lamp is in a second mode, wherein the second mode is a non-operating mode of the UV lamp so that photons are not emitted from the UV lamp. The computed output reading may be based on the deviation and the absolute zero level, so that when the calibrated output reading is computed, the electrical noise seen in the absolute zero level and the photoelectric noise seen in the deviation are considered, and are removed from the calibrated output reading.

Benefiting from the teaching presented in the foregoing description and related accompanying drawings, one skilled in the art regarding these embodiments of the present invention may conceive of many modifications to and other embodiments of the present invention described herein. Therefore, it should be understood that the embodiments of the present invention are not limited to the specific embodiments disclosed herein, and modifications and other embodiments are intended to be included in the scope of the appended claims. Although specific terms are used herein, they are used only in a general and descriptive sense, not for the purpose of limitation.

The invention claimed is:

1. A gas detector for monitoring a target gas, the gas detector comprising:
a gas inlet;
an ultraviolet (UV) lamp;
a pair of electrically biased electrodes provided between the gas inlet and the UV lamp; and
a processor, the processor communicating with the pair of electrically biased electrodes and configured to perform the following:
when the UV lamp is in a first mode and the target gas is prevented from entering the gas inlet, determine a deviation, the first mode of the UV lamp being an operating mode of the UV lamp, so that UV light is emitted therefrom, and the deviation, when the pair of electrically biased electrodes are exposed to the UV lamp in the first mode and are prevented from being exposed to the target gas, being associated with an electrode signal generated by the pair of electrically biased electrodes;
when the UV lamp is in a second mode and photons are not emitted from the UV lamp, the second mode is a non-operating mode thereof, and the processor is configured to determine an absolute zero level when the UV lamp is in the second mode; and
when the gas inlet is open to the target gas, a calibrated output reading based on the deviation is computed, the calibrated output reading, when the pair of electrically biased electrodes are exposed to the UV lamp in the first mode and are exposed to the target gas, being associated with the electrode signal generated by the pair of electrically biased electrodes.

2. The gas detector according to claim 1, wherein the target gas is prevented from entering the gas inlet by providing a calibration filter in the gas detector, inletting a calibration gas, or adopting a combination thereof.

3. The gas detector according to claim 1, wherein the deviation is subtracted from a detector signal obtained from the electrode signal generated by the pair of electrically biased electrodes, when exposed to the UV lamp in the first mode and exposed to the target gas.

4. The gas detector according to claim 3, wherein the electrode signal generated by the pair of electrically biased electrodes, when exposed to the UV lamp in the first mode and prevented from being exposed to the target gas, is formed by at least part of the pair of electrically biased electrodes which are ionized when exposed to the UV light emitted from the UV lamp.

5. The gas detector according to claim 1, wherein the deviation is determined by averaging a plurality of detector signals, and the plurality of detector signals are generated by a plurality of electrode signals generated by the pair of electrically biased electrodes when exposed to the UV lamp in the first mode and prevented from being exposed to the target gas.

6. The gas detector according to claim 1, wherein the calibrated output reading is computed based on the absolute zero level.

7. The gas detector according to claim 1, wherein the processor is configured to determine the deviation after a predetermined period of time, after a specified event occurs, as needed or according to a combination thereof.

8. The gas detector according to claim 1, wherein the processor is configured to update the deviation after a predetermined period of time, after a specified event occurs, as needed or according to a combination thereof.

9. The gas detector according to claim 1, wherein the calibrated output reading represents a concentration of the target gas in an external environment in unit of parts per billion.

10. A gas detector for monitoring a target gas, the gas detector comprising:
a gas inlet;
an ultraviolet (UV) lamp;
a switch used to turn ON and turn OFF the UV lamp, wherein the UV lamp is turned ON when the switch is at a first position and the UV lamp is turned OFF when the switch is at a second position;
a pair of electrically biased electrodes provided between the gas inlet and the UV lamp; and
a processor, the processor communicating with the pair of electrically biased electrodes and comprising:
a deviation determination module, the deviation determination module configured to, when the UV lamp is in a first mode during the switch being at the first position and the target gas is prevented from entering the gas inlet, determine a deviation, the first mode of the UV lamp being an operating mode of the UV lamp, so that UV light is emitted from the UV lamp, and the deviation, when the pair of electrically biased electrodes are exposed to the UV lamp in the first mode and are prevented from being exposed to the target gas, being associated with an electrode signal generated by the pair of electrically biased electrodes, wherein the UV lamp comprises a second mode during the switch being at the second position and photons are not emitted from the UV lamp, and the processor is configured to determine an absolute zero level when the UV lamp is in the second mode; and a calibration module configured to, when the gas inlet is open to the target gas, compute a calibrated output reading based on the deviation, the calibrated output reading, when the pair of electrically biased electrodes are exposed to the UV lamp in the first mode and are exposed to the target gas, being associated with the electrode signal generated by the pair of electrically biased electrodes.

* * * * *